US010226244B2

(12) United States Patent
Lahteenkorva et al.

(10) Patent No.: US 10,226,244 B2
(45) Date of Patent: Mar. 12, 2019

(54) REGULATING DEGRADATION OF SURGICAL IMPLANTS

(71) Applicant: ConMed Corporation, Utica, NY (US)

(72) Inventors: Kimmo Lahteenkorva, Seminole, FL (US); Jeremy Clifford Reedy, Largo, FL (US); Ophir Ortiz, Tampa, FL (US); Christopher Stahle, Belleair, FL (US)

(73) Assignee: ConMed Corporation, Utica, NY (US)

( * ) Notice: Subject to any disclaimer, the term of this patent is extended or adjusted under 35 U.S.C. 154(b) by 169 days.

(21) Appl. No.: 15/282,280

(22) Filed: Sep. 30, 2016

(65) Prior Publication Data

US 2017/0095245 A1 Apr. 6, 2017

Related U.S. Application Data

(60) Provisional application No. 62/236,287, filed on Oct. 2, 2015.

(51) Int. Cl.
*A61B 17/04* (2006.01)
*A61B 17/00* (2006.01)

(52) U.S. Cl.
CPC ...... *A61B 17/0401* (2013.01); *A61B 17/0485* (2013.01); *A61B 2017/00004* (2013.01); *A61B 2017/00477* (2013.01); *A61B 2017/00836* (2013.01); *A61B 2017/00995* (2013.01); *A61B 2017/0403* (2013.01); *A61B 2017/044* (2013.01); *A61B 2017/0409* (2013.01); *A61B 2017/0414* (2013.01); *A61B 2017/0427* (2013.01)

(58) Field of Classification Search
CPC ......... A61F 2210/0009; A61B 17/0401; A61B 2017/00836; A61B 2017/0403; A61B 2017/0409; A61B 2017/0414; A61B 2017/044; A61B 17/809
See application file for complete search history.

(56) References Cited

U.S. PATENT DOCUMENTS

| 6,287,332 B1 | 9/2001 | Bolz et al. | |
|---|---|---|---|
| 2010/0249832 A1* | 9/2010 | Stopek | A61B 17/0401 606/232 |
| 2010/0249838 A1* | 9/2010 | Stopek | A61B 17/0401 606/246 |
| 2010/0249854 A1* | 9/2010 | Thomas | A61B 17/0401 606/301 |

(Continued)

FOREIGN PATENT DOCUMENTS

| CN | 102170921 A | 8/2011 |
|---|---|---|
| WO | WO2009111300 A2 | 9/2009 |

(Continued)

OTHER PUBLICATIONS

International Search and Written Opinion for related PCT/US2016/054877 dated Dec. 8, 2016.

*Primary Examiner* — Katrina Stransky
(74) *Attorney, Agent, or Firm* — Paul Frank + Collins P.C.

(57) ABSTRACT

Embodiments of an implant that is configured with materials to prevent degradation or corrosion. The implant can comprise an elongate body and a degradation-delaying element disposed thereon, where the degradation-delaying element can be configured to reduce or retard corrosion of the elongate body.

20 Claims, 12 Drawing Sheets

(56) References Cited

U.S. PATENT DOCUMENTS

2010/0249944 A1* 9/2010 Thomas ............. A61B 17/0401
623/23.57
2011/0313527 A1* 12/2011 Witte ................. A61B 17/0401
623/11.11
2013/0060348 A1 3/2013 Hodgkinson et al.

FOREIGN PATENT DOCUMENTS

WO    WO2010034098 A1    4/2010
WO    WO2012118846 A1    9/2012

* cited by examiner

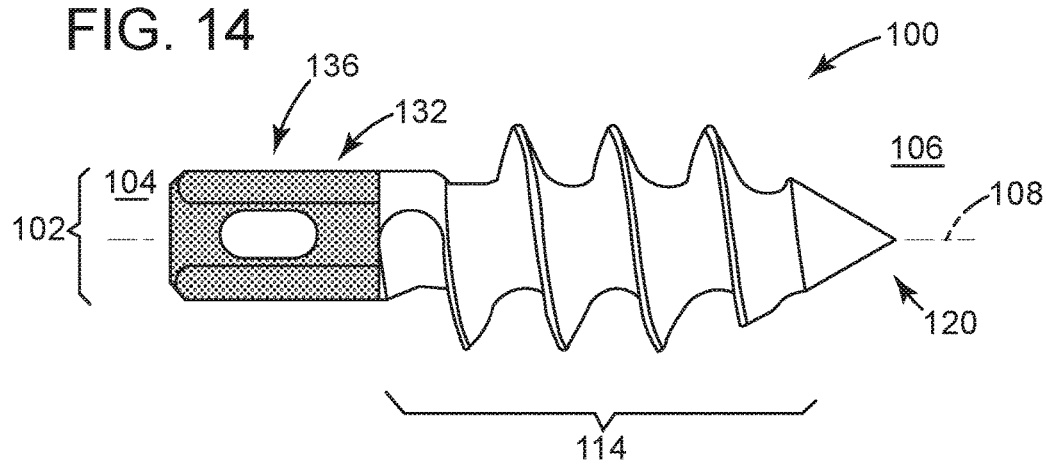
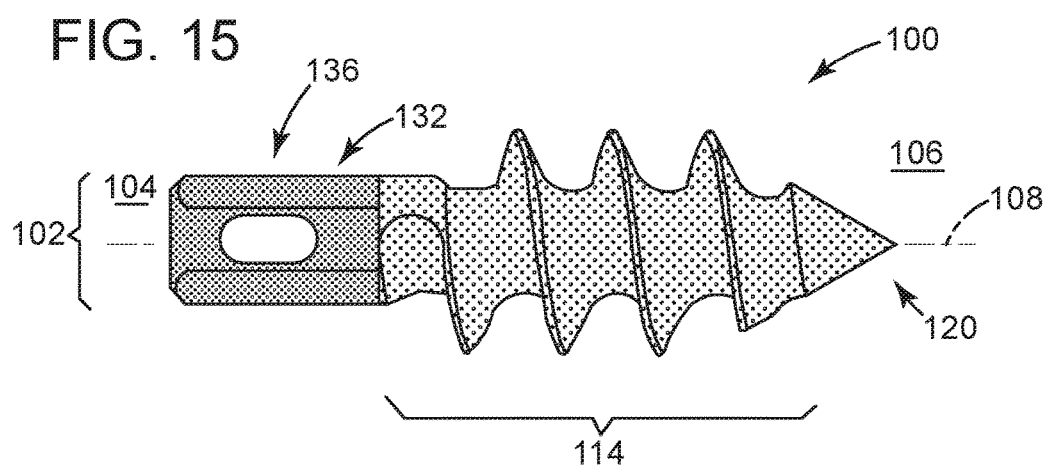
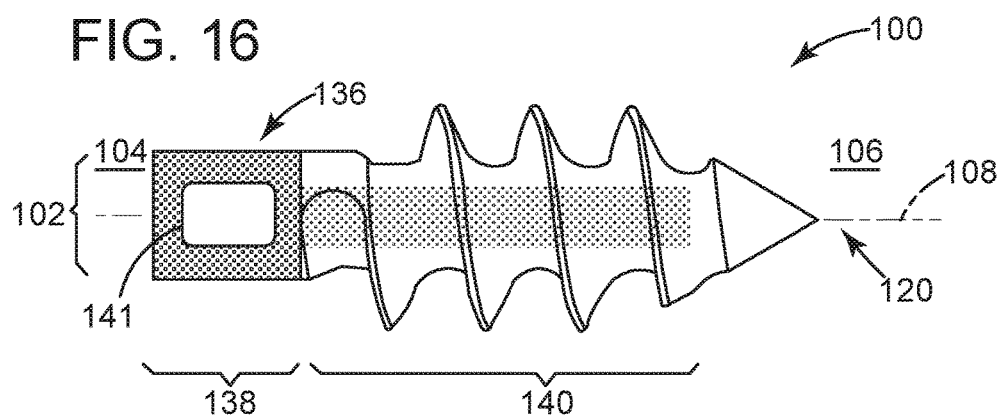

REGULATING DEGRADATION OF SURGICAL IMPLANTS

CROSS-REFERENCE TO RELATED APPLICATIONS

This application claims the benefit of U.S. Provisional Application Ser. No. 62/236,287, filed Oct. 2, 2015, and entitled "REGULATING DEGRADATION OF SURGICAL IMPLANTS," the content of which is incorporated by reference herein in its entirety.

BACKGROUND

Surgical procedures often require an implant to attach tissue or sutures in and/or against a substrate. The substrate may be bone or bony material or soft tissue. A surgeon may use the sutures to capture and retain other objects including tissue. For bone and like bony material, the implant can insert into the bone at a fixation site (e.g., a pre-formed hole in the bone or self-made hole that the implant causes to form in the bone). Suture, graft, or tissue will extend from the implant out of the fixation site. Where the substrate is soft tissue, the implant may reside on a side of the soft tissue so that the suture extends from the implant, through a hole in the tissue, and further beyond the soft tissue on a side opposite the implant.

SUMMARY

The subject matter of this disclosure relates generally to implants, with particular discussion about improvements to regulate degradation of implants that are configured to resorb into the body. These improvements can preserve the structural integrity of critical parts and features on the implants for longer periods of time. The improvements can also reduce the rate of corrosion (e.g., galvanic corrosion) that may occur to implants that are pre-packaged onto an insertion tool and/or tooling prior to use in a surgical procedure.

Some embodiments of the implant may comprise materials that are biocompatible with the human tissues (including bony tissues). Suitable materials may include polymers, polymer blends, polymer composites, and ceramics. The embodiments may also comprise magnesium (Mg) and its alloys ("Mg-alloys"), iron (Fe) and its alloys ("Fe-alloys"), and zinc (Zn) and its alloys ("Zinc-alloys") because these materials exhibit exceptional biocompatibility, mechanical properties, and biodegradation. In some embodiments, the implant may be configured with both polymer-based materials and Mg-based materials, as desired. These configurations may benefit from assembly of the implant from separate pieces or leverage manufacturing techniques (e.g., machining, injection molding, casting, etc.) to allow combinations of pieces that comprises different types of materials.

Some embodiments may include a degradation-delaying element to manage corrosion of Mg-based materials prior to, during, and after deployment. Examples of this degradation-delaying element can include a coating or finish that is disposed on all or part of the Mg-based material. The degradation-delaying element can comprise materials (e.g., polymers, calcium phosphate, and combinations and derivations thereof) that slow down corrosion and degradation of the underlying Mg-based materials. In one implementation, the coating may be deposited onto an area of the implant. This area may be configured with dimensions (e.g., size, thickness, etc.) to manage corrosion and/or degradation of the implant.

BRIEF DESCRIPTION OF THE DRAWINGS

The appended figures illustrate only typical embodiments of the disclosed subject matter and are therefore not to be considered limiting of its scope, for the disclosed subject matter may admit to other equally effective embodiments.

Reference is now made briefly to the accompanying drawings, in which:

FIG. 14 depicts a perspective view of an example of the implant of FIG. 1 that embodies a self-drilling suture anchor;

FIG. 15 depicts the self-drilling suture anchor of FIG. 12;

FIG. 16 depicts the self-drilling suture anchor of FIG. 12;

Figure 1:
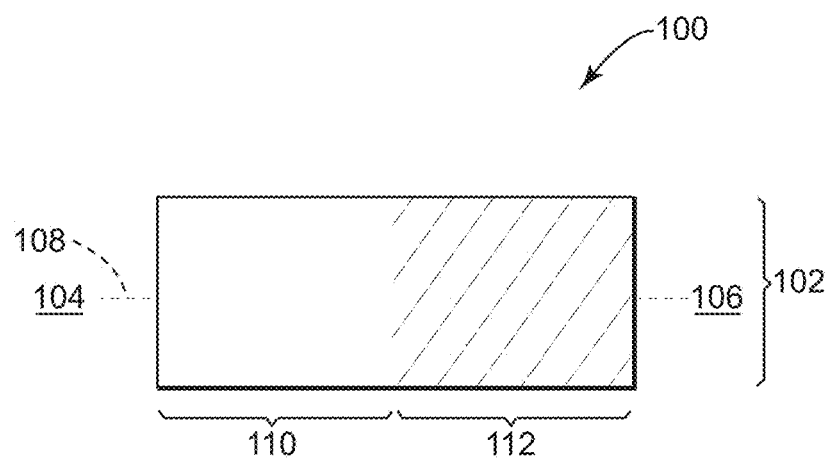
FIG. 1 depicts a schematic diagram of an exemplary embodiment of an implant for use in vivo during surgery.

Where applicable like reference characters designate identical or corresponding components and units throughout the several views, which are not to scale unless otherwise indicated. The embodiments disclosed herein may include elements that appear in one or more of the several views or in combinations of the several views. Moreover, methods are exemplary only and may be modified by, for example, reordering, adding, removing, and/or altering the individual stages.

DETAILED DISCUSSION

The discussion below describes various embodiments of a device for use to secure sutures to target materials, typically bone and bony material. The embodiments are configured to offer different rates of material degradation on the device. In this way, the configurations may keep intact certain critical structure of the implant so as to make the device easier to deploy, to promote better engagement with the target material, or to ensure better retention of the sutures as the device resorbs into the target material. Other embodiments are contemplated within the scope of this disclosure.

FIG. 1 depicts a schematic diagram of an exemplary embodiment of an implant 100 that is configured for use in vivo during surgery. These configurations may be, generally, used in orthapaedic surgery. Examples include suture anchors, nails, pins, interference screws, plates, wedges, and the like. These devices are useful to secure material (e.g., suture, graft, tissue, etc.) securely on the body and, in one implementation, to bone or bony material. The embodiment includes a body member 102 with a first end 104, a second end 106, and a longitudinal axis 108 that extends therebetween. The body member 102 may have one or more sections (e.g., a first section 110 and a second section 112). Each of the sections 110, 112 can exhibit a material property for the body member 102. This material property may define a rate at which the body member 102 degrades and/or breaks down to destroy the structure of the material in the sections 110, 112.

Broadly, the implant 100 may be configured to regulate the rate of degradation of the body member 102 as between the sections 110, 112. These configurations may utilize materials, coatings, coverings, inserts, or like "elements" in (or as part of) the structure of the body member 102. The elements may have structure consistent with manufacturing processes that use spraying, dipping, and/or other deposition techniques to dispose the element onto the body member 102. In some implementations, molding techniques can secure the element to the body member 102 of the implant 100. Suitable molding techniques can include heat staking and overmolding (e.g., single and multi-shot, sequential, etc.). In other implementations, the implant 100 can comprise an insert of material that is different from the material of the body member 102. For example, the body member 102 may comprise Mg-alloy and the insert may comprise calcium phosphate. This recitation of processes and techniques is not exhaustive as this disclosure contemplates many different processes that may be useful to facilitate use of the elements and/or implants contemplated herein.

The "elements," as noted above, may be useful to slow corrosion or degradation of one part of the body member 102 relative to another part. For embodiments of the implant 100 that are meant to resorb into the body, such variations in the rate of degradation may allow, or direct, corrosion and/or degradation of non-critical portions of the body member 102 to occur before critical portions of the body member 102. The critical portions may interface with suture material and/or an insertion tool. The critical portions may also include a tip or end of the implant 100 that is configured to penetrate, puncture, or engage the human body as a surgical site. Often this tip may be configured to self-punch, self-drill, self-tap to create a anchor site in the target material. Features disposed at these critical portions like threads, protrusions, annular rings, and/or snap features may be useful for this purpose.

FIGS. 2, 3, 4, 5, 6, and 7 illustrate various views of an example of the implant 100. This example embodies a suture anchor or like fixation device. Devices of this type may be useful to fix tendons and ligaments to bone. In one implementation, the body member 102 forms an elongate cylinder 114 with an outer surface 116 having threads 118 disposed thereon. At the distal end 106, the elongate cylinder 114 can have a tip 120. One or more apertures (e.g., a first aperture 122 and a second aperture 124) may penetrate into the body member 102 to expose a bore 126 with an inner surface 128. The bore 126 may extend along at least a portion of the longitudinal axis 108, although it may be useful for the bore 126 to extend through the elongate cylinder 114 to create a hollow or cavernous opening in the device. In one implementation, the bore 126 extends from the proximal end 104 and terminates proximate the distal end 106 to form the tip 120. Construction of the bore 126 may allow access into the elongate cylinder 114 to insert or thread suture material into the implant 100. At the proximal end 104, the bore 126 may configure the implant 100 to interface with an insertion tool and/or other implement that facilitates use and deployment of the implant 100 into the human body at the surgical site, as desired.

Figure 2:
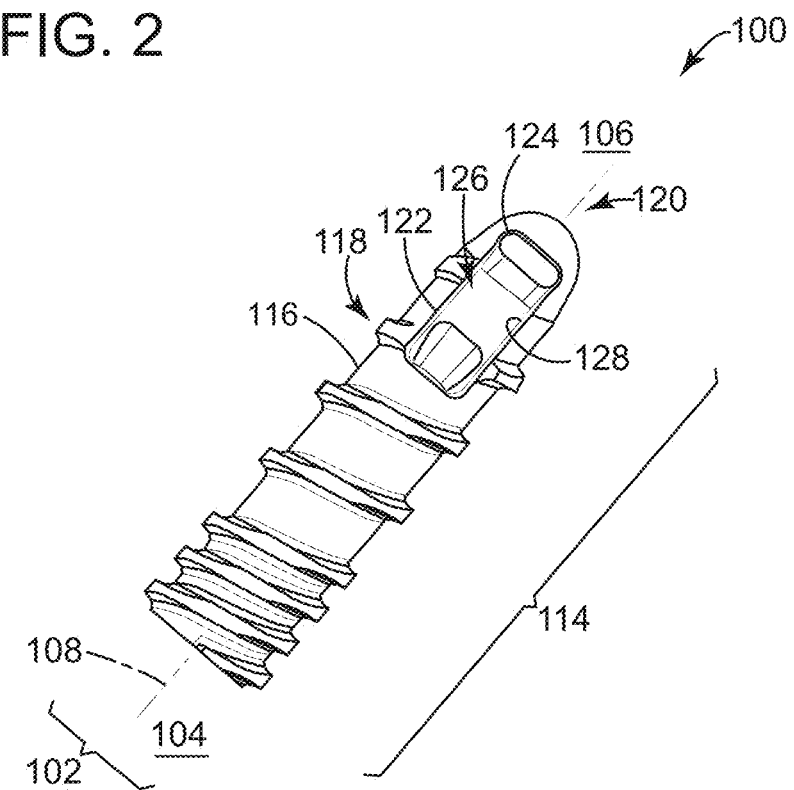
FIG. 2 depicts a perspective view of an example of the implant of FIG. 1 that embodies a suture anchor.
Figure 3:
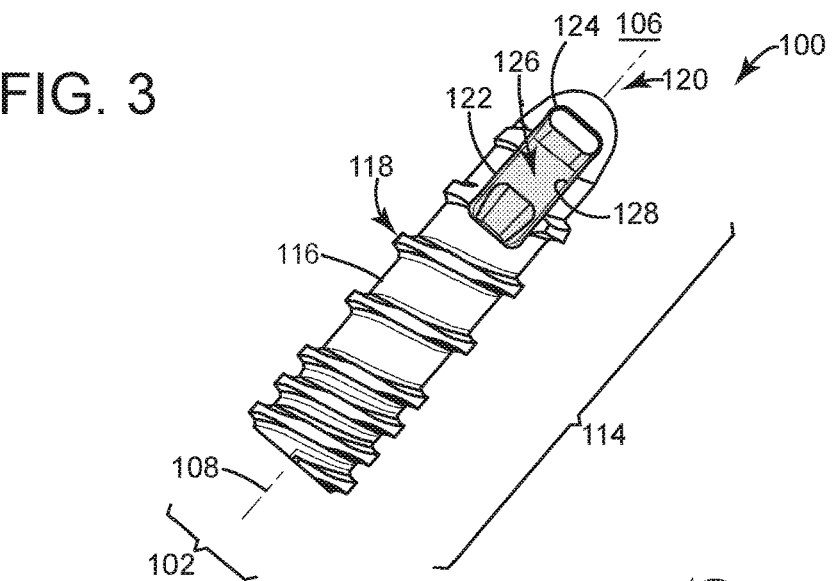
FIG. 3 depicts the suture anchor of FIG. 2.
Figure 4:
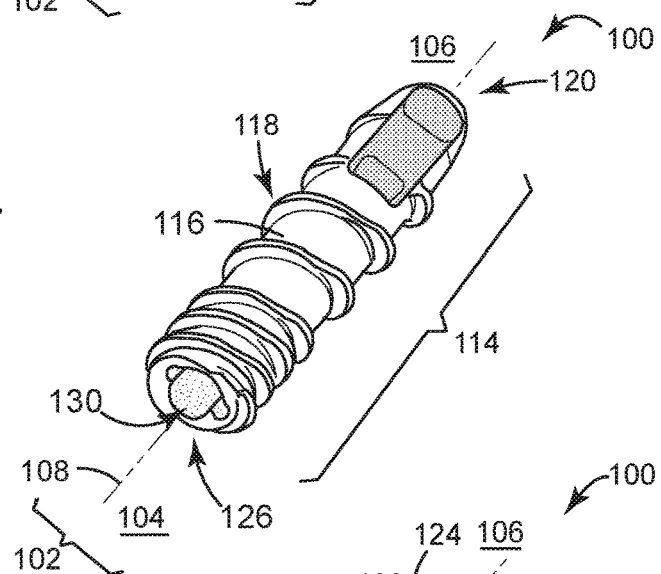
FIG. 4 depicts the suture anchor of FIG. 2.

FIGS. 3 and 4 illustrate a first configuration that can regulate the rate of degradation of the implant 100 of FIG. 2. This first configuration includes a first degradation-delaying element 130 that forms an interior coverage area that covers at least part of the inner surface 128 of the bore 126. The inner coverage area may at least partially circumscribe the longitudinal axis 108. However, full coverage of the bore 126 may benefit the design so as to delay degradation on the inside of the device. As best shown in FIG. 4, the first coverage area may also cover part of the bore 126 at the proximal end 102. Such configurations may cause the element 130 to extend the length of the device along the longitudinal axis 108, for example, from end 102 to end 104. In one construction, the first degradation-delaying element 130 may embody a coating that is disposed on the elongate cylinder 114. This coating may be beneficial to provide full coverage of the inner surface 128 of the bore 126. In another construction, the first degradation-delaying element 130 may embody a sleeve that inserts into the bore 126. Other constructions may leverage manufacturing techniques (e.g., molding or casting) that can form the implant 100 from at least two different materials, wherein at least one of these materials covers or forms a portion of the inner surface 128 of the bore 126.

Figure 5:
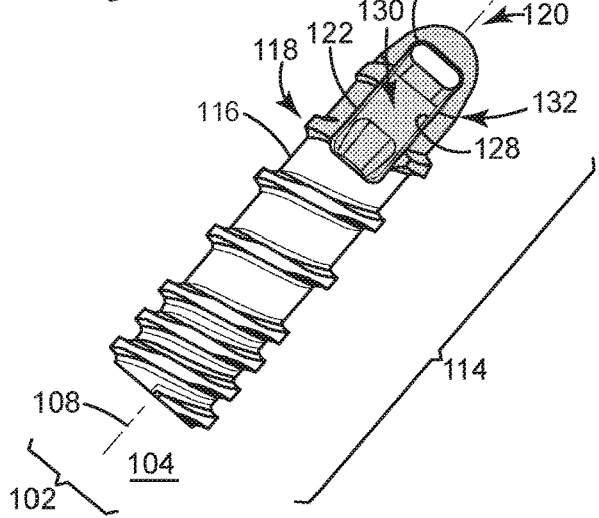
FIG. 5 depicts the suture anchor of FIG. 2.
Figure 6:
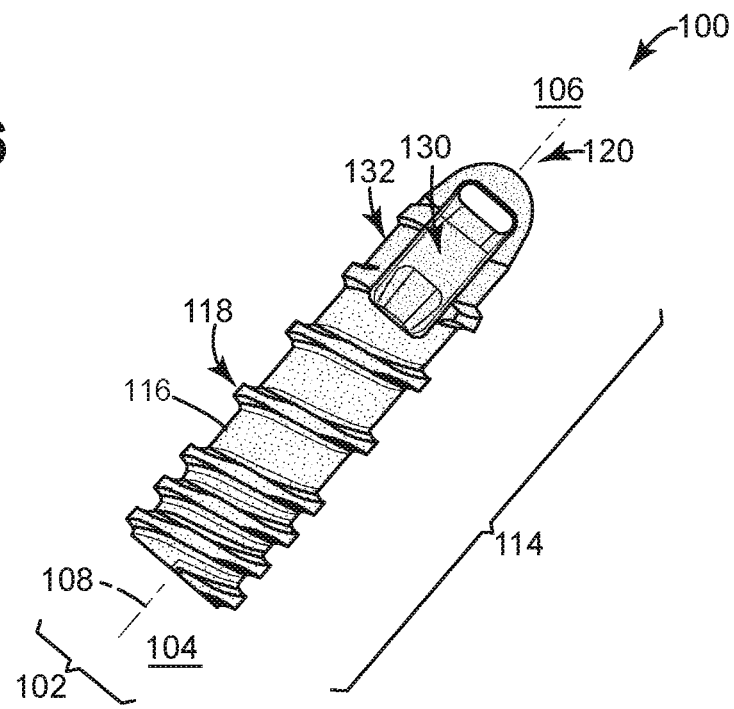
FIG. 6 depicts the suture anchor of FIG. 2.

FIGS. 5 and 6 illustrate a second configuration that can regulate the rate of degradation of the implant 100 of FIG. 2. This second configuration includes a second degradation-delaying element 132 that forms an outer coverage area that covers at least part of the outer surface 116 of the elongate cylinder 114. The implant 100 may include both of the elements 130, 132, possibly formed so that at least part of the inner coverage area and at least part of the outer coverage area are integral or monolithic with one another. The outer coverage area may at least partially circumscribe the longitudinal axis 108. The outer coverage area may also extend along the longitudinal axis 108, covering at least part of the outer surface 116 and/or the threads 118, although both may not be necessary in some implementations. The outer coverage area may also cover the outer surface 118 at the tip 120. FIG. 6 illustrates an example of the implant 100 in which the outer coverage area extends longitudinally to cover the elongate cylinder 114 between the ends 104, 106.

Figure 7:
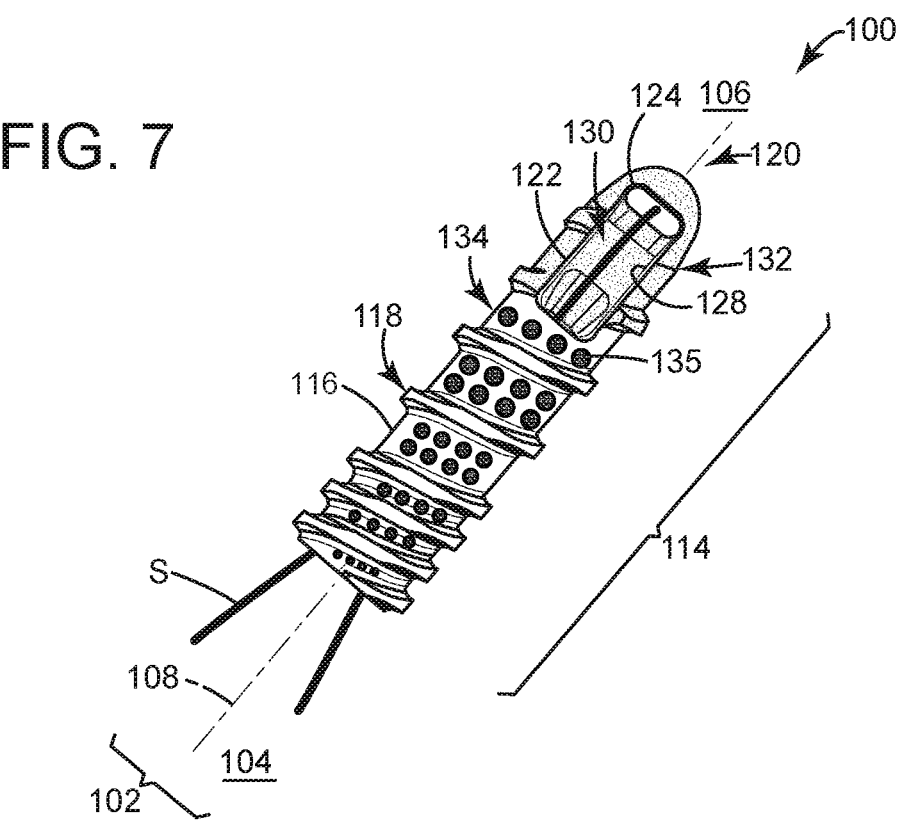
FIG. 7 depicts the suture anchor of FIG. 2.

FIG. 7 illustrates a third configuration that regulates the rate of degradation of the implant 100 of FIG. 2. This third configuration includes a third degradation-delaying element 134 in the form of one or more discrete elements 135 that form the outer coverage area and/or the inner coverage area, as desired. The discrete elements 135 may be arranged in a pattern and/or array. In FIG. 7, the discrete elements 135 are disposed in spaced relation to one another and circumferentially about the longitudinal axis 108. The discrete elements 136 may be circular, although other shapes (e.g., rectangular, square, ellipse, etc.) may also find use to regulate degradation of the implant 100. The implant 100 is configured to receive a suture S. In use, the suture S can insert into the first end 104 and extend through the aperture 124. This configuration allows the suture S to exit the bore 126 (FIG. 2) so that a portion of the suture S resides outside of the implant 100 at time of deployment into bony material.

The elements 130, 132, 134 may leverage certain physical properties to regulate the rate of degradation. These physical properties may include, for example, material thickness. In one example, the material thickness within the inner coverage area or the outer coverage area may be uniform or constant, taking into consideration certain manufacturing tolerances. The material thickness may also vary, wherein the material thickness increases and/or decreases in accordance with a pattern or gradient. The pattern may define a discrete increment or "step" that changes the material thickness, e.g., from a first thickness to a second thickness and vice versa. The gradient may define a linear change in the material thickness or pattern density. Other physical properties may include dimensions for the size and shape of the inner coverage area and the outer coverage area. In one example, these dimensions may correspond with the shape of the discrete elements 136 (FIG. 7). As noted herein, material configurations may also operate to regulate rate of degradation. Exemplary materials, generally, can exhibit a rate of degradation that is less than (or slower than) the material of the elongate body (or implant). These materials can include polymers, zinc, iron, calcium phosphate, but other materials that exhibit suitable rates of degradation may also be useful for this purpose.

Figure 8:
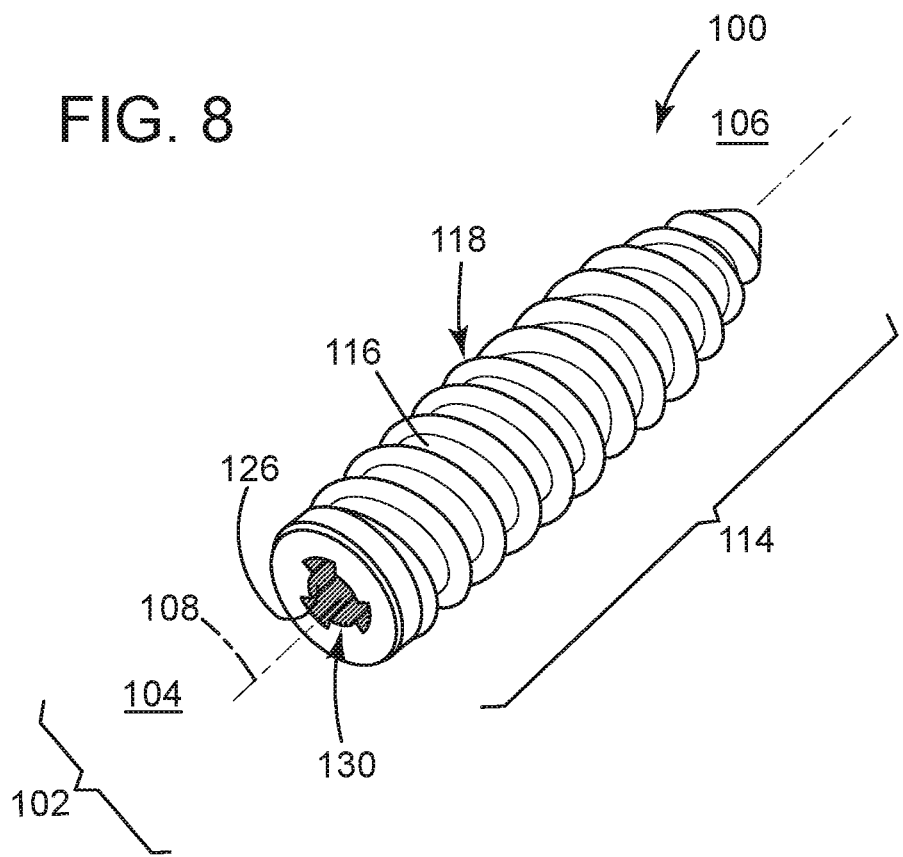
FIG. 8 depicts a perspective view of an example of the implant of FIG. 1 that embodies one example of an interference screw.
Figure 9:
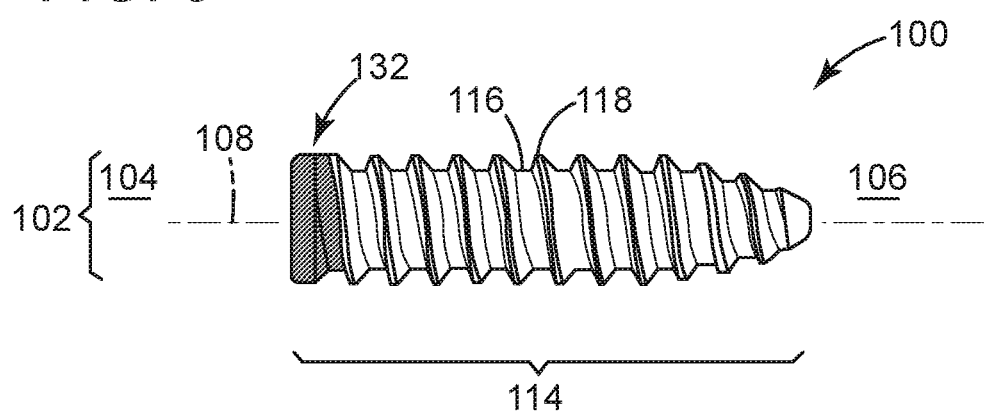
FIG. 9 depicts the interference screw of FIG. 8.

FIGS. 8, 9, 10, and 11 illustrate various views of another example of the implant 100. This example may embody an interference screw, examples of which are useful to pinch or wedge suture, graft, or tissue against the interior of the anchor site (typically a pre-formed hole or aperture in the bone). The threads 118 can be configured to extend generally uniformly along the outer surface 116 so that the screw can advance into the anchor site by turning the device. In FIG. 8, the first degradation-delaying element 130 forms the inner coverage area at least proximate the proximal end 104 of the body member 102. This part of the structure may be critical to engage with the insertion tool. It may be useful for the inner coverage area to extend into the bore 126, as noted above. FIG. 9 shows that the second degradation-delaying element 132 may form the outer coverage area proximate the proximal end 102 of the body member 102. The position of the elements 130, 132 may delay corrosion of the body member 102. This feature may slow the rate of degradation at the interface between the interference screw and an insertion tool (not shown).

Figure 10:
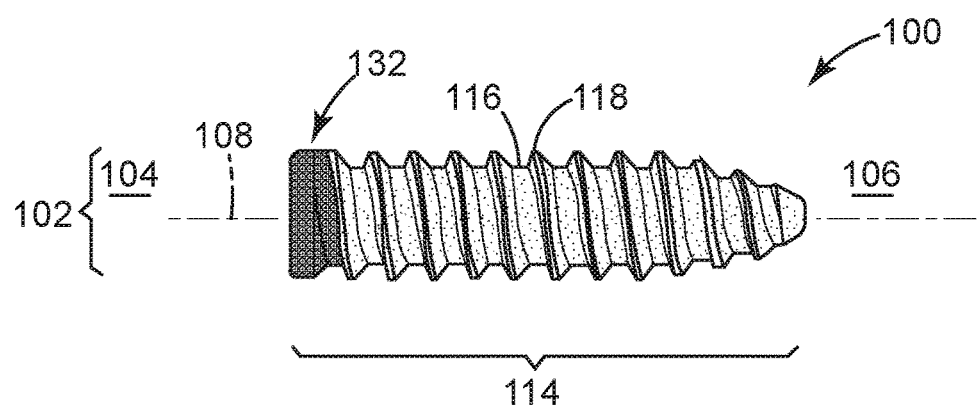
FIG. 10 depicts the interference screw of FIG. 8.
Figure 11:
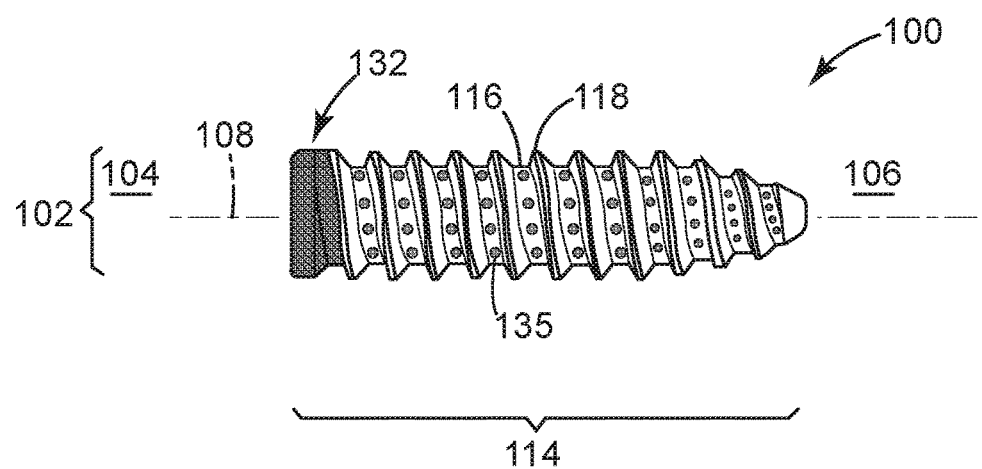
FIG. 11 depicts the interference screw of FIG. 8.

FIG. 10 shows the second degradation-delaying element 132 configured so that the outer coverage area extends longitudinally along the length of the interference screw and, where applicable, at least circumferentially about the longitudinal axis 108. The material thickness of the second degradation-delaying element 132 may be uniform between the ends 104, 106. In other examples, the material thickness may vary between ends 104, 106 and/or circumferentially around the axis 108. In FIG. 11, the interference screw is configured to include the third degradation-delaying element 134 with the discrete elements 135 disposed longitudinally between the threads 118 and radially around the longitudinal axis 108.

Dimensions for the elements 130, 132 may vary across the various examples of the implant 100. These dimensions can impact the "size" of the inner coverage area and the outer coverage area as between the interference screw of FIG. 9 and the suture anchor of FIG. 7. For example, the bore 126 on the interference screw may have a diameter that is smaller than the diameter of the bore 126 on the suture anchor of FIG. 7. The interference screw may also have an outer diameter that is smaller than the outer diameter of the suture anchor of FIG. 7.

Figure 12:
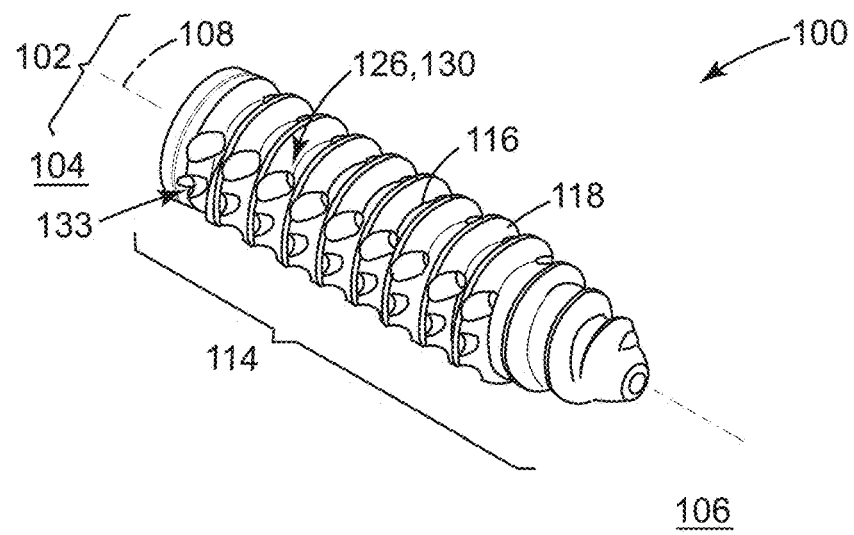
FIG. 12 depicts a perspective view of the implant of FIG. 1 that embodies another example of an interference screw.
Figure 13:
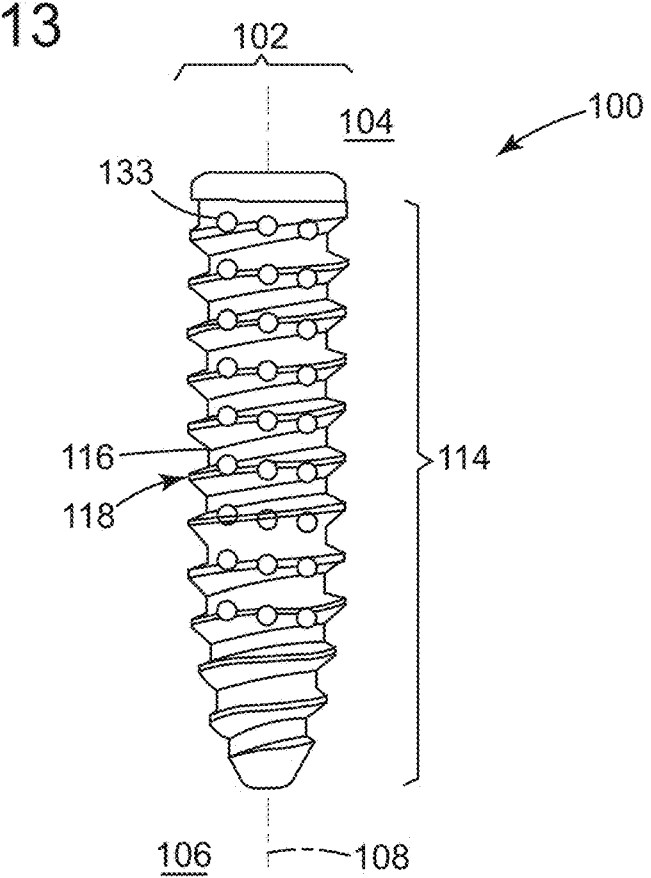
FIG. 13 depicts the interference screw of FIG. 12.

FIGS. 12 and 13 illustrate various views of yet another example of the implant 100. This example also embodies an interference screw. Here, the body member 102 can incorporate one or more radially-extending apertures 133 that expose at least a portion of the bore 126 (FIG. 8). In this example, the body member 102 also includes the first degradation-delaying element 130, which is disposed on the bore 126, either before or after formation of the radially-extending apertures 133. It may be beneficial to include the element 130 as part of a post-manufacture process to allow the element 130 to also cover the inner wall of the radially-extending apertures 133.

The apertures 133 can form openings that are located variously along the length of the body member 102. These openings can populate the outer surface 116. In one implementation, the body member 102 may have one or more arrays of the openings. Within the array, the openings may be spaced apart from one another. This spacing can use different dimensional separation with respect to adjacent apertures 133, as desired. For example, the dimensional separation may be uniform. However, uniform spacing may not always be necessary or preferred and give way to different patterning of the openings on the body member 102. Within the array(s) and/or pattern(s), the openings may have uniform or different diameters, depths, and other physical features. As best shown in FIG. 13, one or more of the radially-extending apertures 133 may form openings that penetrate through body member 102.

Use of the radially-extending apertures 133 may benefit the design and implementation of the implant 100. The apertures 133 can decrease mass, provide openings for bone growth, enhance physiological fluid/cell flux, increase surface area to improve rates of absorption and bioactivity (e.g., osteoconductivity), and increase rate of ethylene oxide sterilization by increasing the rate at which ethylene oxide diffuses post-sterilization.

FIGS. 14, 15, and 16 illustrate various views of yet another example of the implant 100. This example may embody a suture anchor that is configured to thread and/or screw into a bony member. At the distal end 106, the tip 120 may be configured with one or more defined cutting edge(s) that come to a point and/or like invasive feature to penetrate into the bony member. The body member 102 may also include a suture retaining member 136 on the proximal end 104. The suture retaining member 136 may be formed integrally with the elongate cylinder 114 or as a separate piece or "insert" that couples to the elongate cylinder 114. As shown in FIG. 14, the second degradation-delaying element 132 may form the outer coverage area on the suture retaining member 136. The outer coverage area may also encompass at least part of the elongate cylinder 114, either contiguously with the coverage area on the member 136 or as a separate area as contemplated herein. FIG. 15 shows the second coverage area incorporating both the cylinder 114 and the member 136. In one example, the material thickness of the second degradation-delaying element 132 may vary as between the ends 104, 106 and also as between the cylinder 114 and the suture retaining member 136. For example, the material thickness may decrease from the distal end 106 to the proximal end 104.

FIG. 16 shows a construction for the suture retaining member 136. This construction includes one or more portions (e.g., a first or eyelet portion 138 and a second or stiffening portion 140). The eyelet portion 138 may be configured with an aperture 141 to allow suture material to penetrate through the suture retaining member 136. The stiffening portion 140 can extend into the elongate cylinder 114. In use, the member 136 may comprise Mg-alloy to provide mechanical stiffness and rigidity to the polymer construction of the elongate cylinder 114. Using the second degradation-delaying element 132 to cover the exposed portions of the eyelet portion 138 can inhibit and/or decrease galvanic corrosion at the interface with an insertion tool (not shown).

Figure 17:
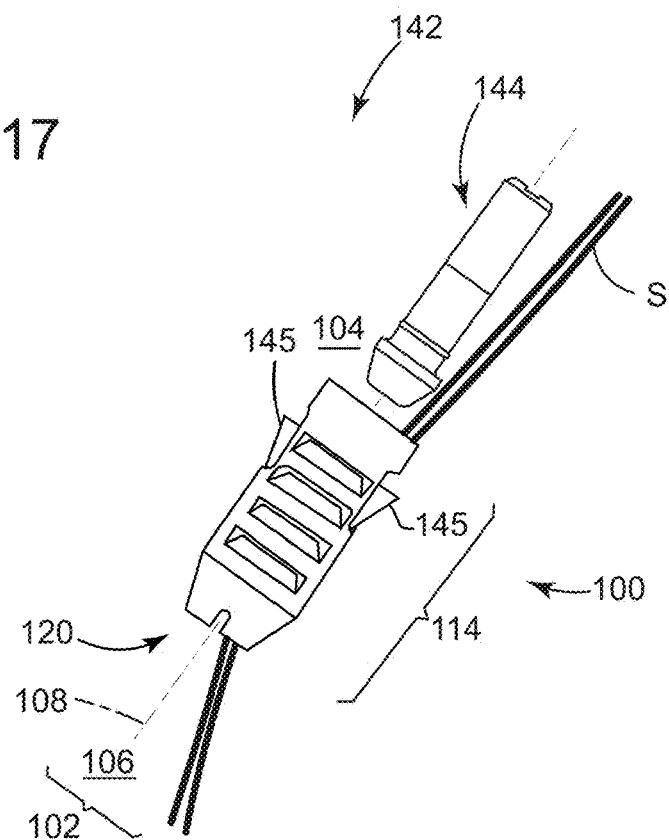
FIG. 17 depicts a perspective view of an example of the implant of FIG. 1 that embodies of an example of a locking suture anchor with articulating tabs.
Figure 18:
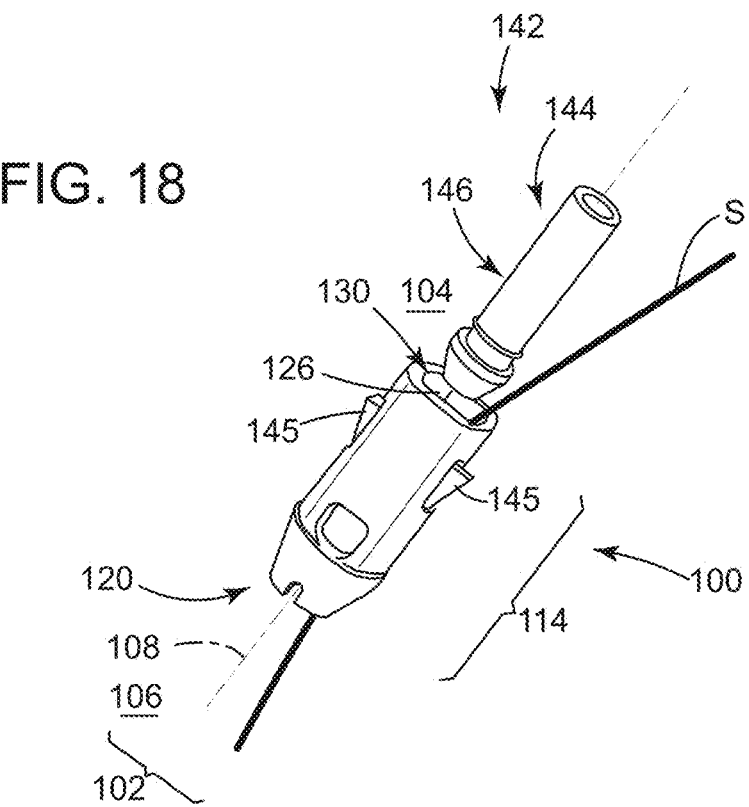
FIG. 18 depicts the locking suture anchor with articulating tabs FIG. 15.

FIGS. 17 and 18 illustrate various views of an example of the implant 100. This example embodies a suture anchor. The suture anchor is shown as part of an insertion system 142 with an insertion tool 144. In one implementation, the suture anchor includes one more tab members 145. The insertion tool 144 can couple with the suture anchor to place and secure suture material S in the body, preferably by deploying the tab members 145 to engage bony material at a surgical site. In one example, the second degradation-delaying element 132 forms the outer coverage area on the elongate cylinder 114.

In FIG. 18, a fourth degradation-delaying element 146 may form a tool coverage area on at least part of the insertion tool 144. The implant 100 may include the first degradation-delaying element 130 to form the interior coverage area on the elongate cylinder 114. In use, the insertion tool 144 can insert into a position in the bore 126. This position can locate the tool coverage area in contact with the interior coverage area to reduce and/or retard galvanic corrosion of the elongate cylinder 114 prior to deployment of the suture anchor during surgery.

Figure 19:
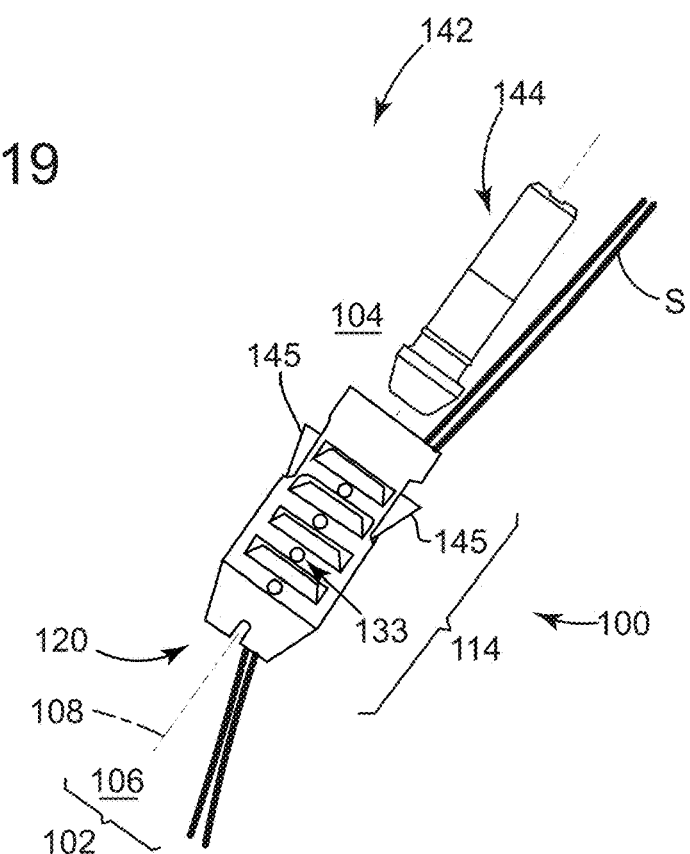
FIG. 19 depicts a perspective view of an example of the implant of FIG. 1 that embodies of another example of a locking suture anchor with articulating tabs
Figure 20:
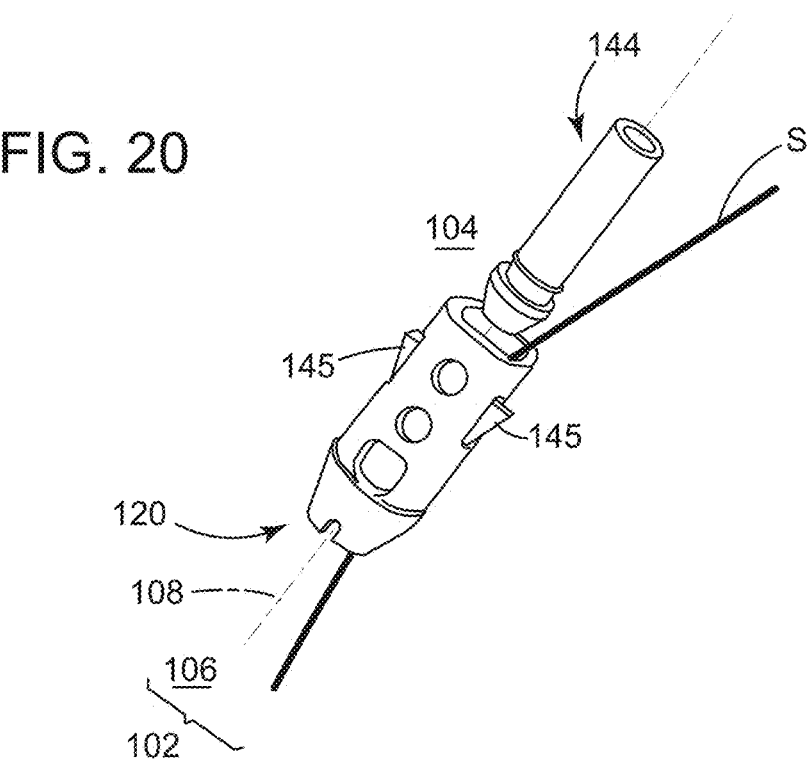
FIG. 20 depicts the locking suture anchor with articulating tabs FIG. 19.

FIGS. 19 and 20 illustrate various views of an example of the implant 100. This example also embodies a suture anchor. Here, the body member 102 includes the radially-extending apertures 133. As best shown in FIG. 20, the radially-extending apertures 133 can vary in size (e.g., diameter). This example utilizes apertures 133 with diameters that increase longitudinally from the distal end 104 to the proximal end 106.

Figure 21:
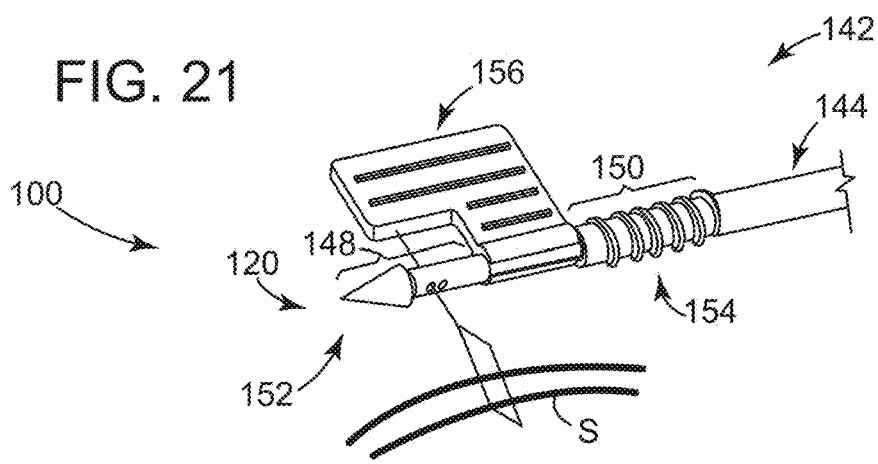
FIG. 21 depicts a perspective view of an example of the implant of FIG. 1 that embodies a self-punching suture anchor.
Figure 22:
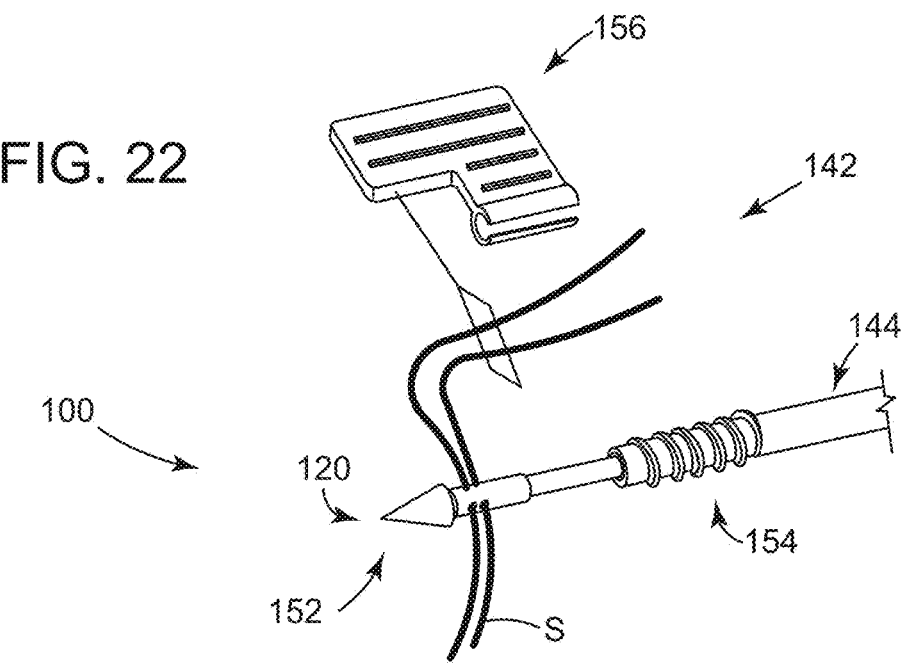
FIG. 22 depicts the self-punching suture anchor FIG. 17.
Figure 23:
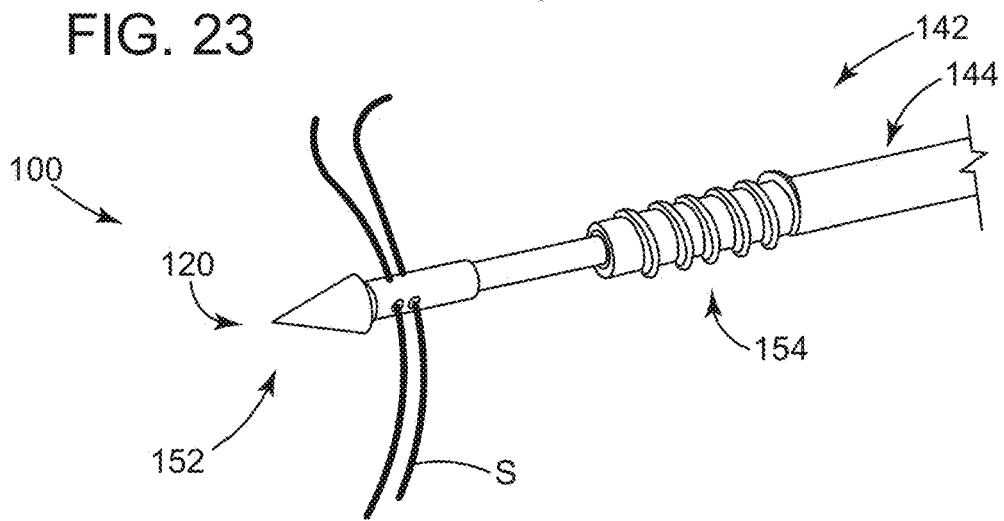
FIG. 23 depicts the self-punching suture anchor FIG. 17.

FIGS. 21, 22, 23, 24, and 25 illustrate various views of still another example of the implant 100. This example embodies a self-punching anchor or anchor system. In this example, the body member 102 may include a plurality of parts (e.g., a first part 148 and a second part 150). The first part 148 can embody a punching member 152 with the tip 120. The second part 150 can form a threaded body 154 with the outer surface 116 and threads 118 disposed thereon. The system 142 may also include a threader 156. In use, an end user can employ the threader 156 to pull the suture S into the punching member 152 (FIGS. 21, 22, and 23). One or more of the insertion tool 144, the first part 148, the second part 150, and the threader 156 may deploy the degradation-delaying elements as noted herein.

Figure 24:
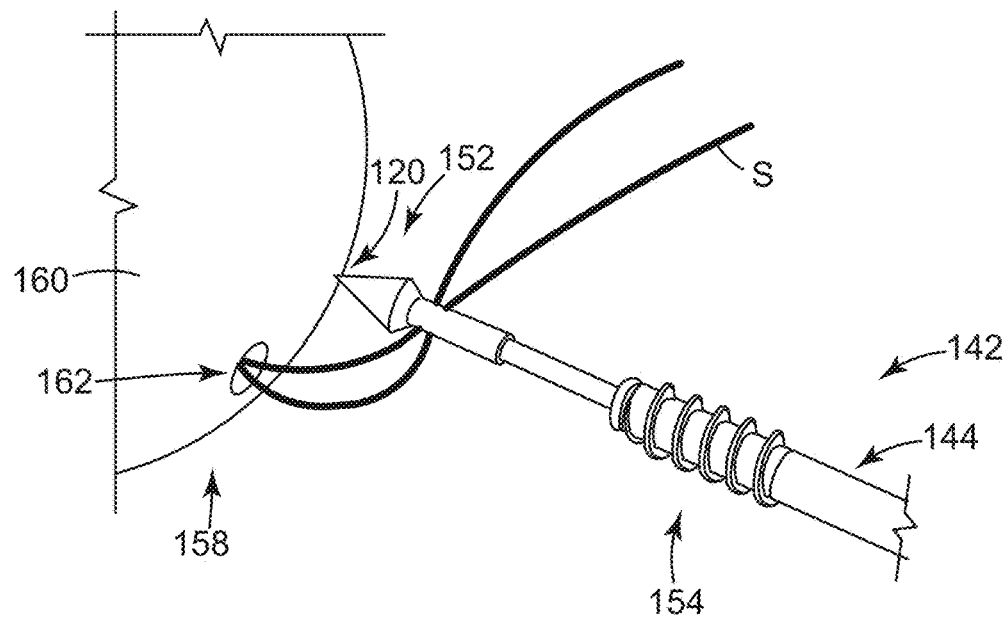
FIG. 24 depicts the self-punching suture anchor FIG. 17.
Figure 25:
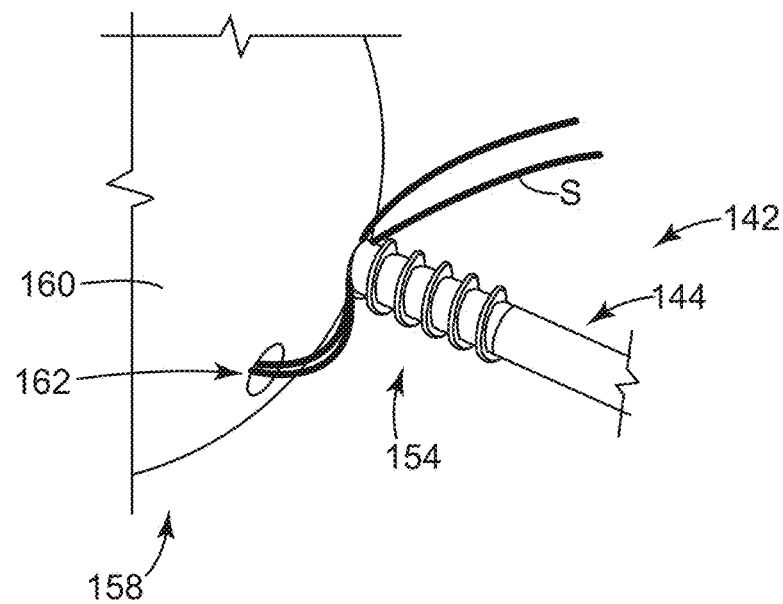
FIG. 25 depicts the self-punching suture anchor FIG. 17.

FIGS. 24 and 25 show the insertion system 144 in position at a surgical site 158 on a bony member 160. The surgical site 158 is prepared with a suture hole 162, typically a bore that enters the bony member 160. In one implementation, the bore may penetrate through the bony member 160 to allow suture S to extend out of suture hole 162. The surgeon can locate the tip 120 of the puncturing member 152 proximate the suture hole 162. By applying a driving force to the insertion tool 144, the surgeon can drive the puncturing member 152 into the bony member 160. The surgeon can also thread the threaded body 154 into the resulting hole to secure the suture S in the bony member 160. In use, a surgical procedure can include stages for deploying a surgical implant having an elongate, cylindrical body and a degradation-delaying element disposed thereon, wherein the degradation-delaying element has a rate of degradation that is less than the rate of degradation of material of the surgical implant.

All the embodiments and processes described above may be altered within the scope of the present invention to accommodate different size and strength requirements based on the variables provided above.

As used herein, an element or function recited in the singular and proceeded with the word "a" or "an" should be understood as not excluding plural said elements or functions, unless such exclusion is explicitly recited. Furthermore, references to "one embodiment" of the claimed invention should not be interpreted as excluding the existence of additional embodiments that also incorporate the recited features.

This written description uses examples to disclose the subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

In light of the foregoing discussion, the improvements herein can maintain structure of implants that is critical to ensure that suture, graft, or tissue is secure to bone and bony material. The degradation elements can be used to modify the rate of degradation of the body as between different parts of the device. This feature is beneficial to avoid, for example, galvanic corrosion (and like corrosive phenomenon) that may alter the structure of implants as packaged or after the implant deploys into the target material at the anchor site. In this regard, the examples below include certain elements or clauses one or more of which may be combined with other elements and clauses describe embodiments contemplated within the scope and spirit of this disclosure.

What is claimed is:

1. An implant, comprising:
   an elongate body with an outer surface and a bore forming an inner surface; and
   a coating disposed on the elongate body,
   wherein the coating is configured to retard corrosion of a first area of the elongate body, and
   wherein the first area is found on the outer surface in a form of a plurality of discrete shapes, each surrounded by areas of the elongated body, and each spaced apart from one another on the outer surface of the elongate body.

2. The implant of claim 1, wherein the the coating covers at least part of the bore.

3. The implant of claim 1, wherein the coating further covers at least part of the outer surface of the elongate body that is not part of the plurality of discrete, circular shapes.

4. The implant of claim 1, wherein the plurality of discrete shapes are disposed in an array, the array extending longitudinally and radially about the outer surface of the elongate body.

5. The implant of claim 1, further comprising a radially-extending aperture that penetrates the elongate body to expose the bore.

6. The implant of claim 5, wherein the coating is disposed on a surface of the radially-extending aperture.

7. The implant of claim 1, wherein the elongate body is configured for use in orthopedic procedures.

8. The implant of claim 1, wherein the elongate body has threads on the outer surface.

9. The implant of claim 1, wherein the elongate body has a tip configured to self-form a hole in bone.

10. The implant of claim 1, wherein the discrete shapes are found between threads on the outer surface.

11. The implant of claim 1, wherein the discrete shapes are circular.

12. The implant of claim 1, wherein the coating uniformly covers a second area at one end of the elongate body devoid of the plurality of discrete shapes.

13. The implant of claim 1, wherein the coating uniformly covers a second area in a bore in the elongate body.

14. The implant of claim 1, wherein the coating uniformly covers a second area on the outer surface at an end of the elongate body having an opening to a bore in the elongate body.

15. The implant of claim 1, wherein the coating covers a second area that includes threads on the outer surface.

16. A method, comprising:
on a surgical implant:
forming a coating on the surgical implant, the coating having a rate of degradation that is less than the rate of degradation of material of the surgical implant,
wherein the coating covers an area on an outer surface of the surgical implant in a form of a plurality of discrete shapes, each surrounded by areas of the elongated body, and each spaced apart from one another on the outer surface of the surgical implant.

17. The method of claim 16, further comprising:
using the coating to cover at least part of an inner surface area formed by a bore in the surgical implant.

18. A surgical kit, comprising:
an insertion tool;
a surgical implant disposed on the insertion tool, the surgical implant having a body that can communicate with the insertion tool
wherein the body of the surgical implant comprises a coating at a first area disposed between the body and the insertion tool and a second area on an outside surface of the surgical implant in a form of a plurality of discrete shapes, each surrounded by areas of the elongated body, and each spaced apart from one another on the outer surface of the surgical implant,
wherein the coating has material properties that are different from material properties of the body and the insertion tool so as to have a rate of degradation that is less than the rate of degradation of both the insertion tool and the body.

19. The surgical kit of claim 18, wherein the coating is disposed on the body of the surgical implant.

20. The surgical kit of claim 18, wherein the body of the surgical implant comprises a bore with an opening to receive the insertion tool, and wherein the coating is disposed at the opening.

* * * * *